(12) United States Patent
Yoon et al.

(10) Patent No.: US 6,384,212 B1
(45) Date of Patent: May 7, 2002

(54) PROCESS FOR PREPARING CEPHALOSPORIN ANTIBIOTICS USING NEW THIAZOLE COMPOUND

(75) Inventors: Dae-chul Yoon, Gunpo; Seung Won Yoo, Ansan; Dong Gyun Shin, Kyunggi-Do; Myoung Ki Lee, Seoul; Mi Soon Park; Yoon Seok Lee, both of Ansan; Yoon Seok Song, Shiheung; Ju Cheol Lee, Gunpo; Sang Mi Oh, Ansan, all of (KR)

(73) Assignee: Hanmi Fine Chemicals Co., Ltd., Kyunggi-do (KR)

( * ) Notice: Subject to any disclaimer, the term of this patent is extended or adjusted under 35 U.S.C. 154(b) by 0 days.

(21) Appl. No.: 09/564,980

(22) Filed: May 4, 2000

(30) Foreign Application Priority Data

Mar. 20, 2000 (KR) ............................. 00-14076

(51) Int. Cl.$^7$ .................. C07D 501/24; C07D 501/34; C07D 501/46
(52) U.S. Cl. .................. 540/222; 540/228; 540/225
(58) Field of Search ................ 540/222, 225, 540/228

(56) References Cited

U.S. PATENT DOCUMENTS

| | | | |
|---|---|---|---|
| 4,258,041 A | | 3/1981 | O'Callaghan et al. |
| 4,423,213 A | | 12/1983 | Takaya et al. |
| 4,939,250 A | * | 7/1990 | Lotus |
| 4,960,889 A | | 10/1990 | Takaya et al. |
| 5,110,921 A | | 5/1992 | Takaya et al. |

FOREIGN PATENT DOCUMENTS

| | | | |
|---|---|---|---|
| EP | 101148 | * | 2/1984 |
| GB | 2 052 490 | | 1/1981 |
| KR | 84001827 B1 | | 10/1984 |
| KR | 84001987 B1 | | 10/1984 |
| KR | 84001988 B1 | | 10/1984 |
| KR | 84001989 B1 | | 10/1984 |
| KR | 84001990 B1 | | 10/1984 |
| KR | 87001807 B1 | | 10/1987 |
| KR | 93007810 B1 | | 8/1993 |
| KR | 00127113 B1 | | 10/1997 |

| | | | |
|---|---|---|---|
| WO | 98/31685 | | 7/1998 |

OTHER PUBLICATIONS (1) Hideaki Yamanaka et al., The Journal of Antibiotics, vol. 38, pp. 1738–1751.

* cited by examiner

Primary Examiner—Mark L. Berch
(74) Attorney, Agent, or Firm—Venable; Richard D. Schmidt

(57) ABSTRACT

The present invention relates to a new, simple, and easy process for preparing cephalosporin antibiotics of the following formula (I), such as ceftazidime and cefixime. The process comprises acylating a 7-amino cephalosporanic acid derivative of the following formula (III) with a crystalline aminothiazole compound of the following formula (II):

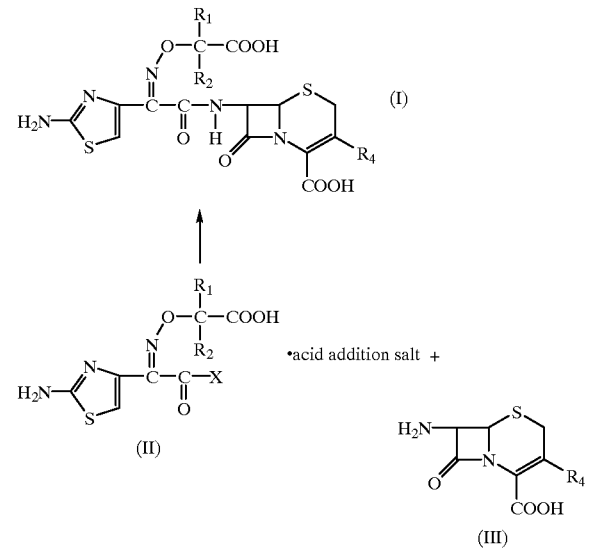

wherein $R_1$ and $R_2$ are the same or different and independently represent H, a $C_{1-4}$ alkyl or $C_{3-5}$ cycloalkyl group, $R_4$ represents acetoxymethyl, methylpyridine, or vinyl, X represents chlorine or bromine, and the acid in the acid addition salt represents an inorganic acid, such as hydrochloric acid, or an organic acid, such as formic acid or acetic acid.

7 Claims, No Drawings

PROCESS FOR PREPARING CEPHALOSPORIN ANTIBIOTICS USING NEW THIAZOLE COMPOUND

BACKGROUND OF THE INVENTION

1. Field of the Invention

The present invention relates in general to a new, simple, and easy process for preparing cephalosporin antibiotics including ceftazidime, cefixime, and the like. More particularly, the present invention relates to a process for the preparation of cephalosporin antibiotics of the following formula (I), in which a 7-amino cephalosporanic acid derivative of the following formula (III) is acylated by reaction with a new crystalline aminothiazole derivative of the following formula (II) in a solvent:

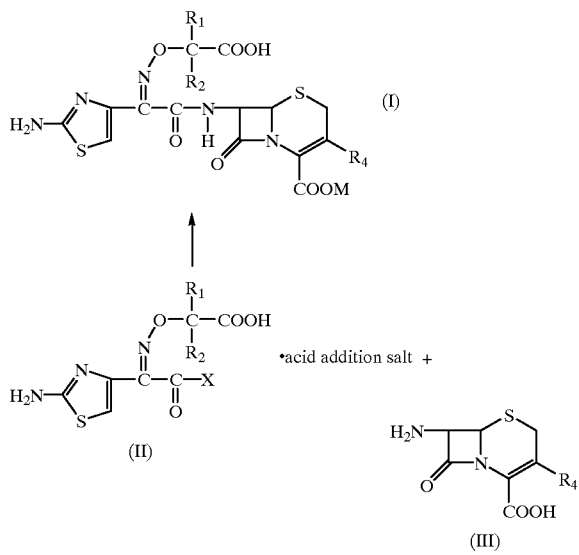

wherein $R_1$ and $R_2$ are the same or different and independently represent H, an alkyl group of 1 to 4 carbon atoms, or a cycloalkyl group of 3 to 5 carbon atoms, etc., $R_4$ represents acetoxymethyl, pyridiniummethyl, or vinyl, COOM is COO⁻ when $R_4$ is pyridiniummethyl and COOH otherwise, and X represents chlorine or bromine. Moreover, the acid in the acid addition salt as shown in the formula (II) represents an inorganic acid, such as hydrochloric acid, hydrobromic acid, sulfuric acid, or perchloric acid, etc., or an organic acid, such as formic acid, acetic acid, trifluoroacetic acid, propionic acid, methanesulfonic acid, or benzenesulfonic acid, etc.

2. Description of the Prior Art

Processes for the preparation of cephalosporin antibiotics of the above formula (I), including ceftazidime and cefixime, were disclosed in several literatures and patents, for example, U.S. Pat. No. 4,258,041; Austrian Patent Publication Nos. 86-2427 and 86-2428; *J. of Antibiotics*, Vol.38, pp. 1738, 1985; and Korean Patent Publication Nos. 84-1827, 84-1987, 84-1988, 84-1989, 84-1990, 87-1807, and 93-7810.

In the above prior processes, an amino group of a 3-cephem compound represented by the following formula (I-1) is acylated by reaction with a 2-aminothiazol carboxylic acid of the following formula (I-2) or a salt or reactive derivative thereof to produce the cephalosporin derivative of the formula

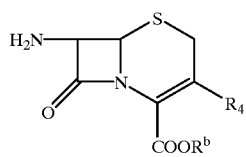

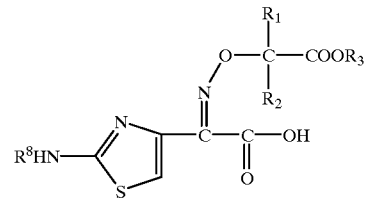

where $R_1$, $R_2$, and $R_4$ have the same meanings as described above, $R_3$ is a carboxy protecting group, $R^a$ is hydrogen or an amino protecting group, $R^b$ is hydrogen or a carboxy protecting group, such as diphenylmethyl or p-nitrobenzene.

U.S. Pat. No. 4,258,041, and Korean Patent Publication No. 84-1827, etc. describe processes employing acid chloride of the organic acid (I-2) in the acylation reaction with the 7-amino cephalosporin derivative of the formula (I-1). According to these processes, the organic acid (I-2) is conventionally protected on an amino group of its thiazole ring, and then converted to its acid chloride with thionyl chloride, phosphorus oxychloride, or phosphorus pentachloride, etc. Thereafter, the resulting acid chloride of the organic acid (I-2) is reacted with the 7-amino cephalosporanic acid derivative, followed by removing the protecting group on the amino group of the thiazole ring. However, these processes have disadvantages in that they are carried out under strict reaction conditions, and further require a step of protecting the amino group of the thiazole ring and a step of removing the protecting group on the amino group. In addition, another drawback with these processes is that the aminothiazole compound activated with unstable acid chloride is acylated as such without being subjected to an isolation step, such that by-products are significantly produced during the acylation reaction owing to the unstable acid chloride.

Austrian Patent Publication Nos. 86-2427 and 86-2428, and WO No. 98-31685, etc. disclose processes in which a reactive ester of the organic acid (I-2) is prepared and acylated. In this acylation, the reactive ester of the organic acid (I-2) may be reacted with the 7-aminocephalosporin derivative without the protecting group on the amino group of its thiazole ring. However, it is necessary for these processes to remove a protecting group on a carboxy group of the aminothiazole compound (I-2) after the acylation reaction, in order to give the final desired compound.

In addition, there are also known other processes employing a reactive amide or a mixed acid anhydride, but they have drawbacks similar to those in the above processes.

Therefore, in the case of carrying out the acylation reaction using the reactive derivative (e.g., the acid chloride) as described above, the amino and carboxyl groups of the compound of the formula (I-2) must be protected with $R^a$ other hand, in the case of using the reactive ester, the preparation of the reactive ester must be carried out in a state where the amino group is not protected, but the carboxyl group is protected with $R_3$. As a result, all the processes according to the prior art have a drawback in that the deprotection must be carried out after the acylation reaction.

SUMMARY OF THE INVENTION

We have discovered that, when an aminothiazole compound represented by the following formula II was acylated by reaction with a 7-amino cephalosporanic acid derivative represented by the following formula (III) in a solvent as indicated in the following reaction scheme, a desired compound could be directly obtained in a high yield in a simple and easy way without a need of the deprotection after the acylation reaction, whereby we have perfected the present invention based on this discovery:

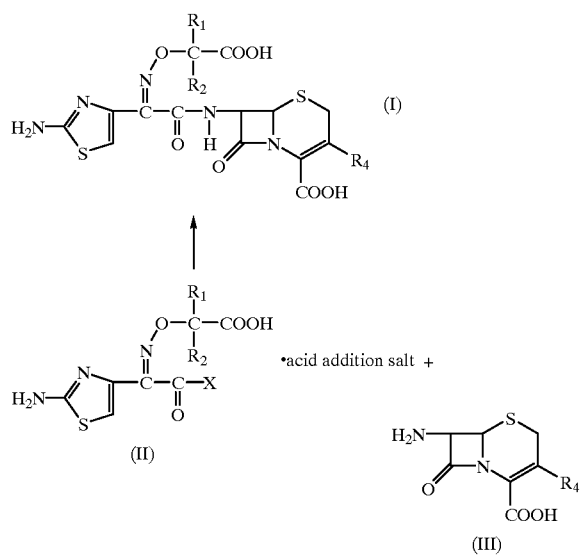

wherein $R_1$, $R_2$, $R_4$, and the acid addition salt have the same meaning as defined above.

It is therefore an object of the present invention to provide a process for preparing cephalosporin antibiotics including ceftazidime and cefixime, etc., using a new aminothiazole compound represented by the formula (II).

DETAILED DESCRIPTION OF THE PREFERRED EMBODIMENTS

The foregoing and other objects, features and advantages of the invention will be apparent to those skilled in the art to which the present invention relates from reading the following specification.

The aminothiazole compound of the formula (II) used as the starting material in the practice of the present invention is a new material and a reactive derivative in the form of a crystalline acid chloride. Thus, this is more stable and can be stored over a lengthy period of time at a low temperature and room temperature, as compared with the conventional acid chloride. Moreover, the process of the present invention produces little or no by-products in the acylation reaction of the 7-aminocephalosporin derivative with the compound of the formula (II), and is also relatively short in reaction time. Additionally, the process of the present invention employing this compound of the formula (II) does not require the removal of the protecting group after the acylation, and allows the desired compound to be directly obtained after the acylation. As a result, the process of the present invention makes the acylation reaction more economical and also simple and easy.

The new aminothiazole derivative of the formula (II) is described in detail in Korean Patent Application No.2000-11127 (Filing date: Mar. 6 2000; Name of Applicant: HANMI FINE CHEMICALS, CO., LTD; and Title: New thiazole compounds and a process thereof), the disclosure of which is incorporated herein by reference. Moreover, among the derivatives of the formula (III), a 3-vinyl-7-aminocephalosporanic acid and a 3-pyridiniummethyl-7-aminocephalosporanic acid mentioned herein are known compounds and described in detail in several literatures, for example, U.S. Pat. No. 4,423,213, Korean Patent No. 127, 113, and British Patent No. 2,052,490, the disclosure of which is incorporated herein by reference.

In the acylation reaction according to the present invention, the compound of the formula (II) is used in the amount of 1.0 to 2.0 equivalents, and preferably 1.2 to 1.4 equivalents, relative to the compound of the formula (III).

The solvent which can be used in the practice of the present invention includes, for example, dichloromethane, dichloroethane, chloroform, acetonitrile, tetrahydrofuran, N,N-dimethylacetamide, N,N-dimethylformamide, methanol, ethanol, or a combination thereof. However, a solution adjuvant, such as N,O-bistrimethylsilylacetamide, trimethylchlorosilane, or trimethyliodosilane, etc., may also be used in combination with the solvent in the present invention depending on the kind of the 7-cephalosporin derivative.

The solvent is used in the amount of 5 ml to 30 ml, and preferably 10 ml to 15 ml, relative to 1 g of the compound of the formula (II). The acylation reaction according to the present invention is preferably carried out at a temperature of −10° C. to 30° C.

The acylation reaction of the present invention is generally carried out without the use of a base, although an organic or inorganic base may also be used depending on the 7-aminocephalosporin derivative. If used, the base is used in the amount of 1.0 to 3.0 equivalents. Examples of the organic base which can be used in the present invention include tri-(n-butyl)amine, diisopropylethylamine, pyridine, dicyclohexylamine, and the like. Moreover, the acylation reaction may also be carried out in a mixed solution of a basic aqueous solution and the organic solvent, with the basic aqueous solution being preferably an aqueous solution of sodium hydrogen carbonate, potassium hydrogen carbonate, sodium carbonate, or sodium hydroxide, etc.

In this acylation reaction, water and the organic solvent are preferably used in the volume of 10 times to 20 times relative to the compound of the formula (II), with the volume ratio of water to the organic solvent being 1/4 to 1/10.

As described above, the process for the preparation of the cephalosporin derivative is characterized in that the compound of the formula (III) is reacted with the new thiazole compound of the formula (II), as the reactive organic acid derivative, to give the cephalosporin derivative of the formula (I). Such a process does not require the deprotection step and is reduced in production step, as compared with the processes according to the prior art. Furthermore, as the reactive acid derivative used in the process of the present invention is the acid chloride of the stable crystalline form, the acylation reaction with the compound of the formula (II) can be completed clean in a quantitative view with little or no production of by-products. In addition, the compound of the formula (II) can be stored in the form of acid chloride and is thus easy to use. As a result, the present invention provides the more inexpensive and new acylation process for the preparation of the cephalosporin derivatives having the compound of the formula (II) at a 7-position.

The following examples are for illustration purposes only and in no way limit the scope of this invention.

EXAMPLE 1

Preparation of 7-{2-(2-aminothiazol-4-yl)-2-(Z)-(2-carboxyprop-2-oxyimino)acetamido}-3-(1-pyridiniummethyl) -ceph-3-em-4-carboxylate dihydrochloride(ceftazidime dihydrochloride)

To 100 ml of acetonitrile which was cooled down to 0 to 5° C., 10 g of 7-amino-3-(1-pyridiniummethyl)-ceph-3-em-carboxylate dihydrochloride was added, and 5 ml of N,O-bistrimethylsilylacetamide was then slowly added dropwise over 30 minutes. After adding 9.4 g of (Z)-(2-carboxyprop-2-oxyimino)-2-aminothiazole-4-yl)-acetylchloride monohydrochloride, the resulting solution was stirred for 30 minutes, and 20 ml of 35% concentrated hydrochloric acid was then added to the stirred solution, followed by adding 50 ml of diethylether. Next, the solution was stirred for 10 minutes, and an aqueous layer was then separated and collected. After 100 ml of acetone was added to the aqueous layer and the mixture was stirred at room temperature for 5 to 6 hours, the deposited crystal was filtered. The filtered crystal was washed with 50 ml of isopropyl alcohol, and then with 20 ml of acetone, and dried, thereby giving 12.4 g (84% yield) of the title compound as a white solid.

$^1$NHR :(d, DMSO-$d_6$):9.6(d, 1H, —CONH—), 9.0(d, 2H, pyridinium proton), 8.6(t, 2H, pyridinium proton), 8.2(t, 2H, pyridinium proton), 6.8(s, 1H, aminothiazole proton), 5.9 (dd, 1H, $C_7$—H), 5.6(ABq, 2H, —$CH_2$—), 5.2(d, 1H, $C_6$—H), 3.5(ABq, 2H, $C_2$—H), 1.4(s, 6H, —$C(CH_3)_2$)

EXAMPLE 2

Preparation of 7-{2-(2-aminothiazole-4-yl)-2-(Z)-(2-carboxyprop-2-oxyimino)acetamido}-3-(1-pyridiniummeth yl)-ceph-3-em-4-carboxylate pentahydrate(ceftazidime penta hydrate)

To 100 ml of dichloromethane, 10 g of 7-amino-3-(1-pyridiniummethyl)-ceph-3-em-4-carboxylate hydroiodide was added, and 4 ml of triethylamine was then added dropwise at a temperature of 0 to 10° C. to ensure the dissolution of the hydroiodide. To which, (Z)-(2-carboxyprop-2-oxyimino)-2-(2-aminothiazole-4-yl)-acetylchloride monohydrochloride was added three or four times for 30 minutes in such a fashion that the totally added amount thereof corresponds to 9.4 g. The resulting mixture was then stirred at a temperature of 0 to 10° C. for 30 minutes. The stirred solution was added with 50 ml of water to be separated into two layers. Next, an aqueous layer was collected, to which 2 g of activated carbon was added. The solution was stirred for 30 minutes, and the stirred solution was filtered by a siliceous earth to remove the activated carbon. The resulting solution was adjusted to pH 3.8 with a 2N-hydrochloric acid solution, and left to stand at 5° C. for 12 hours. The resulting crystal was filtered, and washed with ice-water and acetone, in sequence, and then dried, thereby giving 11.8 g (80% yield) of the title compound as a white solid.

$^1$NHR :(d, DMSO-$d_6$): 9.5(d, 1H, —CONH—), 9.4(d, 2H, pyridinium proton), 8.6(t, 2H, pyridinium proton), 8.2(t, 2H, pyridinium proton), 7.3(s, 2H, —$NH_2$), 6.7(s, 1H, amino-thiazole proton), 5.7(dd, 1H, $C_7$—H), 5.5(ABq, 2H, —$CH_2$—), 5.1(d, 1H, $C_6$—H), 3.3(ABq, 2H, $C_2$—H), 1.4(s, 6H, —$C(CH_3)_2$)

EXAMPLE 3

Preparation of 7-[2-(2-aminothiazole-4-yl)-2-(Z)-(carboxymethoxyimino)acetamido]-3-vinyl-3-cephem-4-carboxylic acid trihydrate (cefixime)

10 g of 7-amino-3-vinyl-3-cephem-4-carboxylic acid was suspended in 100 ml of dichloromethane, and to which, 10 ml of N,O-bistrimethylsilylacetamide was added dropwise to ensure the dissolution of the carboxylic acid. At a temperature of 20 to 30° C., 14 g of (Z)-2-(2-carboxymethoxyimino)-2-(2-aminothiazole-4-yl) acetylchloride monohydrochloride was added in parts and the resulting solution was stirred. After this, 50 ml of a saturated aqueous solution of sodium hydrogen carbonate and 100 ml of isopropylether were sequentially added, and the resulting solution was stirred for 10 minutes and separated into two layers, the aqueous layer of which was collected. The aqueous solution was adjusted to pH 2.0–2.5 with 6 N-hydrochloric acid solution and left to cool at a temperature of 0 to 5° C. for one hour, followed by filtering the deposited crystal. The filtered crystal was washed with 150 ml of cold water and 200 ml of acetone, in sequence, and then dried, thereby giving 19.5 g (87% yield) of the title compound as a pale yellow solid. Melting Point(° C.): 200–230(decomposition)

$^1$NHR :(d, $D_2O$-$NaHCO_3$); 3.7(s, 2H), 4.8–5.8(m, 5H), 6.9(dd, 1H, J=12 Hz, 18 Hz)

As apparent from the above description and Examples, the present invention provides the process for the preparation of the cephalosporin derivative, wherein the compound of the formula (III) is reacted with the new thiazole compound of the formula (II), as the reactive organic acid derivative, to give the cephalosporine derivative of the formula (I). Such a process does not require the deprotection step and is reduced in production step, as compared with the processes according to the prior art. Furthermore, as the reactive organic acid derivative used in the process of the present invention is the acid chloride of the stable crystalline form, it allows the acylation reaction with the compound of the formula (III) to be completed clean in a quantitative view with little or no production of by-products. In addition, the compound of the formula (II) can be stored in the form of acid chloride and is thus easy to use. As a result, the present invention provides the more inexpensive and new acylation process for the preparation of the cephalosporine derivatives having the compound of the formula (II) at a 7-position.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:
1. A process for the preparation of cephalosporin antibiotics represented by the following formula (I), in which an acid addition salt of a crystalline aminothiazole compound represented by the following formula (II) is acylated by reaction with a 7-aminocephalosporanic acid derivative represented by the following formula (III) in a solvent:

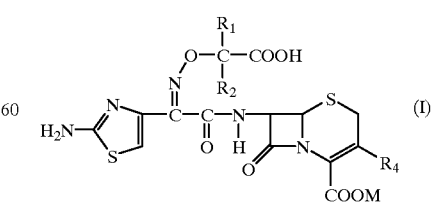

-continued

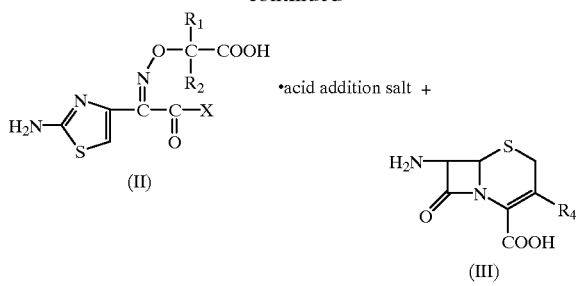

wherein $R_1$ and $R_2$ are the same or different and independently represent H, an alkyl group of 1 to 4 carbon atoms, or a cycloalkyl group of 3 to 5 carbon atoms, $R_4$ represents acetoxymethyl, pyridiniummethyl, or vinyl, COOM is $COO^-$ when $R_4$ is pyridiniummethyl and COOH otherwise, X represents chlorine or bromine, and the acid in the acid addition salt represents an inorganic acid selected from the group consisting of hydrochloric acid, hydrobromic acid, sulfuric acid, and perchloric acid, or an organic acid selected from the group consisting of formic acid, acetic acid, trifluoroacetic acid, propionic acid, methanesulfonic acid, and benzenesulfonic acid.

2. The method of claim 1, wherein the 7-aminocephalosporanic acid derivative is selected from the group of 7-amino-3-(1-pyridiniummethyl)-ceph-3-em-carboxylate hydrochloride and 7-amino-3-(1-pyridiniummethyl)-ceph-3-em-carboxylate hydroiodide.

3. The method of claim 1, wherein $R_4$ is vinyl.

4. The method of claim 1, wherein the solvent is selected from the group consisting of dichloroethane, chloroform, tetrahydrofuran, N,N-diethylacetamide, dichloro methane, acetonitrile, N,N-dimethylformamide, acetone, water, methanol, ethanol, and a combination thereof.

5. The method of claim 4, wherein the solvent is used in a combination with a solution adjuvant selected from the group consisting of N,O-bistrimethylsilylacetamide, trimethylchloro silane, and trimethyliodosilane.

6. The method of claim 1, wherein the acylation reaction is carried out in the presence of an additional organic base selected from the group consisting of triethylamine, tri-(n-butyl)amine, dicyclohexylamine, pyridine, and diisopropyl ethylamine.

7. The method of claim 4, wherein the acylation reaction is carried out in a mixed solution of a basic aqueous solution and the organic solvent, with the basic aqueous solution being an aqueous solution of an inorganic base selected from the group consisting of sodium hydrogen carbonate, potassium hydrogen carbonate, sodium carbonate, and sodium hydroxide.

* * * * *